(12) United States Patent
Clark

(10) Patent No.: US 9,354,151 B2
(45) Date of Patent: May 31, 2016

(54) APPARATUS FOR FOUR-POINT BEND TESTING

(71) Applicant: ROLLS-ROYCE PLC, London (GB)

(72) Inventor: Brynley Clark, Bristol (GB)

(73) Assignee: ROLLS-ROYCE plc, Derby (GB)

( * ) Notice: Subject to any disclaimer, the term of this patent is extended or adjusted under 35 U.S.C. 154(b) by 0 days.

(21) Appl. No.: 14/631,280

(22) Filed: Feb. 25, 2015

(65) Prior Publication Data
US 2015/0268144 A1    Sep. 24, 2015

(30) Foreign Application Priority Data

Mar. 21, 2014 (GB) .................................. 1405073.6

(51) Int. Cl.
*G01N 3/20* (2006.01)
*G01N 3/32* (2006.01)
*G01M 5/00* (2006.01)

(52) U.S. Cl.
CPC .. *G01N 3/20* (2013.01); *G01N 3/32* (2013.01); *G01M 5/0016* (2013.01); *G01N 2203/0023* (2013.01); *G01N 2203/0282* (2013.01)

(58) Field of Classification Search
CPC ......... G01N 3/20; G01M 5/0016; F16C 35/06
USPC .................................................... 73/852, 849
See application file for complete search history.

(56) References Cited

U.S. PATENT DOCUMENTS

| | | | | |
|---|---|---|---|---|
| 3,031,886 A | * | 5/1962 | Larsson .................... | G01N 3/34 73/810 |
| 3,142,174 A | * | 7/1964 | Baker ...................... | G01N 3/20 269/8 |
| 3,170,321 A | * | 2/1965 | Sullivan .................... | G01N 3/34 73/812 |
| 3,665,751 A | * | 5/1972 | Paine ....................... | G01N 3/32 374/47 |
| 4,589,288 A | * | 5/1986 | Porter ...................... | G01N 3/20 73/849 |
| 4,677,856 A | * | 7/1987 | Fischer .................... | G01N 3/00 73/850 |

(Continued)

FOREIGN PATENT DOCUMENTS

| | | |
|---|---|---|
| DE | 103 29 012 A1 | 1/2005 |
| GB | 2 324 876 A | 11/1998 |

(Continued)

OTHER PUBLICATIONS

Sep. 11, 2014 Search Report issued in British Application No. 1405073.6.

*Primary Examiner* — Lisa Caputo
*Assistant Examiner* — Tran M Tran
(74) *Attorney, Agent, or Firm* — Oliff PLC

(57) ABSTRACT

A rig for testing an aerofoil component in four-point bending, which includes first and second fixtures movable relative to each other to apply a cyclically varying load to opposing aerofoil surfaces of the component. The first fixture has two first loading formations positioned to apply the load to one surface of the component, the formations being spaced apart in the spanwise direction of the component. The second fixture has two second loading formations positioned to apply the load to the other surface of the component, which are also spaced apart in the spanwise direction of the component and positioned relative to the first loading formations to apply the load in a four-point bending arrangement. The second fixture is continuously adjustable so that its loading formations move relative to each other in the direction of application of the load to balance the load between the formations during the cyclical load variation.

13 Claims, 1 Drawing Sheet

(56) References Cited

U.S. PATENT DOCUMENTS

| | | | | |
|---|---|---|---|---|
| 4,730,498 A * | 3/1988 | Blanch | G01N 3/20 | 73/852 |
| 4,875,376 A * | 10/1989 | Fischer | G01N 3/00 | 73/850 |
| 4,941,359 A * | 7/1990 | Quinn | G01N 3/20 | 73/851 |
| 4,986,132 A * | 1/1991 | Calomino | G01N 3/20 | 73/852 |
| 4,991,446 A * | 2/1991 | Bechtel | G01N 3/20 | 73/849 |
| 5,056,361 A * | 10/1991 | Roberts | G01M 9/062 | 73/147 |
| 5,111,688 A * | 5/1992 | Houghton | G01N 3/08 | 73/159 |
| 5,231,882 A * | 8/1993 | Bertele | G01N 3/32 | 73/852 |
| 5,280,730 A * | 1/1994 | Peres | G01N 3/04 | 73/846 |
| 5,424,634 A * | 6/1995 | Goldfarb | G01N 3/36 | 324/763.01 |
| 5,503,024 A * | 4/1996 | Bechtel | G01N 3/20 | 73/849 |
| 5,847,283 A * | 12/1998 | Finot | G01N 3/20 | 73/800 |
| 5,905,205 A * | 5/1999 | Clay | G01N 3/08 | 73/819 |
| 6,484,567 B1 * | 11/2002 | Hajduk | G01N 3/24 | 73/54.23 |
| 6,505,129 B2 * | 1/2003 | Starostovic | G01N 3/20 | 702/36 |
| 6,644,101 B2 * | 11/2003 | Hajduk | G01N 3/24 | 73/54.37 |
| 6,655,194 B2 * | 12/2003 | Hajduk | G01N 3/24 | 73/54.37 |
| 6,668,231 B2 * | 12/2003 | Stylios | G01N 3/20 | 162/198 |
| 6,668,622 B2 * | 12/2003 | Hajduk | G01N 3/24 | 73/54.23 |
| 6,681,618 B2 * | 1/2004 | Hajduk | G01N 3/24 | 73/54.02 |
| 6,880,409 B2 * | 4/2005 | Kawabe | G01N 3/24 | 73/856 |
| 6,931,942 B2 * | 8/2005 | Uhlik | G01N 3/20 | 73/853 |
| 7,047,794 B2 * | 5/2006 | Hajduk | G01N 3/24 | 73/54.23 |
| 7,201,064 B2 * | 4/2007 | Doak | G01N 3/20 | 73/788 |
| 7,302,860 B1 * | 12/2007 | Uhlik | G01N 3/20 | 73/853 |
| 7,510,085 B2 * | 3/2009 | Akaike | G01N 33/34 | 209/509 |
| 7,516,644 B2 * | 4/2009 | Wong | G01N 3/20 | 73/12.06 |
| 7,543,507 B2 * | 6/2009 | Li | G01B 3/18 | 324/763.01 |
| 7,546,775 B2 * | 6/2009 | Chinavare | G01N 3/32 | 73/849 |
| 7,621,187 B2 * | 11/2009 | Chalmers | G01N 3/32 | 73/159 |
| 7,690,265 B2 * | 4/2010 | Cipra | G01N 3/20 | 73/849 |
| 7,866,483 B2 * | 1/2011 | Akaike | G01N 33/34 | 209/509 |
| 7,974,803 B2 * | 7/2011 | Logan | G01N 33/46 | 702/104 |
| 8,082,802 B1 * | 12/2011 | Sadegh | G01N 3/08 | 73/760 |
| 8,365,610 B2 * | 2/2013 | Decraecker | | 73/794 |
| 8,443,678 B2 * | 5/2013 | Nardi | G01N 3/04 | 73/760 |
| 8,461,860 B2 * | 6/2013 | Kim | G01M 5/005 | 324/762.01 |
| 8,621,935 B2 * | 1/2014 | Foltz | G01N 3/04 | 73/841 |
| 8,850,898 B2 * | 10/2014 | Johnsen | G01N 3/02 | 73/849 |
| 8,863,585 B2 * | 10/2014 | Wang | G01N 3/34 | 73/812 |
| 9,091,617 B2 * | 7/2015 | Edelman | G01N 3/04 | |
| 9,097,621 B2 * | 8/2015 | Osborne | G01M 5/005 | |
| 9,103,751 B2 * | 8/2015 | Negro | G01N 3/04 | |
| 2014/0245833 A1 * | 9/2014 | Bruchhausen | G01N 3/12 | 73/571 |

FOREIGN PATENT DOCUMENTS

| | | | | |
|---|---|---|---|---|
| GB | 2324876 A | * | 11/1998 | G01N 3/32 |
| JP | S61-142439 A | | 6/1986 | |

\* cited by examiner

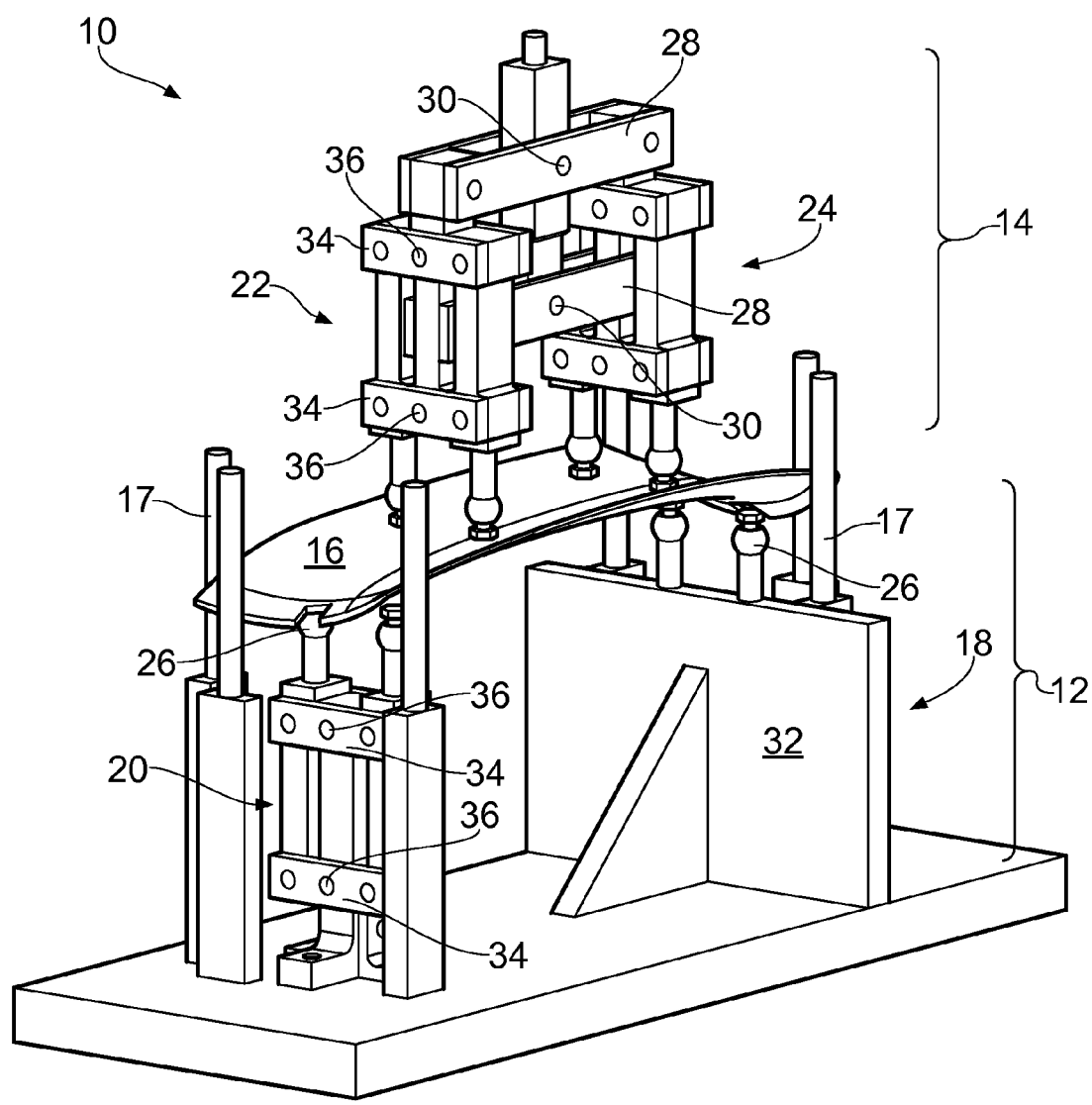

APPARATUS FOR FOUR-POINT BEND TESTING

FIELD OF THE INVENTION

The present invention relates to a rig for testing an aerofoil component in four-point bending.

BACKGROUND OF THE INVENTION

Gas turbine engine aerofoil components (i.e. blades or vanes) are traditionally assessed for high cycle fatigue (HCF) by carrying out fatigue tests on sample components. This entails clamping the vane/blade at its end fixings and then mechanically exciting one of the component's modal frequencies. The exciting force can be provided by a mechanical shaker or by a pulsed or constant air jet. Large amplitudes of vibration are generally required in order to produce desired HCF failures.

Organic matrix composite (OMC) aerofoil components are becoming more widely incorporated into gas turbine engines. However, conventional methods of exciting blade/vane vibration modes can be inadequate for such components. In particular, OMCs tend to have high intrinsic damping and hence it can be difficult to excite their vibration modes to high enough amplitudes to cause HCF failure.

SUMMARY OF THE INVENTION

It would be desirable to provide an alternative testing method, particularly for OMC aerofoil components.

Accordingly, in a first aspect, the present invention provides a rig for testing an aerofoil component in four-point bending, the rig including first and second fixtures movable relative to each other to apply a cyclically varying load to opposing aerofoil surfaces of the aerofoil component,
  the first fixture having two first loading formations which are positioned to apply the load to one of the aerofoil surfaces of the component, the first loading formations being spaced apart in the spanwise direction of the component, and
  the second fixture having two second loading formations which are positioned to apply the load to the other aerofoil surface of the component, the second loading formations also being spaced apart in the spanwise direction of the component and being positioned relative to the first loading formations to apply the load in a four point bending arrangement;
  wherein the second fixture is continuously adjustable so that its loading formations move relative to each other in the direction of application of the load to balance the load between the loading formations during the cyclical load variation.

In general, blades/vanes do not have symmetric cross sections and hence they deform in an uneven way. Advantageously, the continuous adjustability of the second fixture can ensure that all the loading formations carry equal load throughout the loading cycle. The four-point bending arrangement ensures that the maximum bending stress in the component occurs in the centre section of the component away from the fixtures. The rig also allows high loads to be applied.

The rig may have any one or, to the extent that they are compatible, any combination of the following optional features.

Conveniently, the second loading formations may be supported at opposite ends of a set of first balancing beams of the second fixture, the load being transmitted to the second loading formations through the set of first balancing beams, which rock to produce the relative movement of the second loading formations in the direction of application of the load.

Each loading formation may have two pads which make loading-contact with that formation's aerofoil surface at respective positions spaced apart in the chordwise direction of the component. Each of three of the loading formations can then be continuously adjustable so that its pads move relative to each other in the direction of application of the load to balance that loading formation's share of the load between the pads during the cyclical load variation. The use of such pads allows the load to applied more uniformly across the chordwise direction of the component. Conveniently, each of the three adjustable loading formations can have a respective set of second balancing beams which support that loading formation's pads at opposite ends thereof, the adjustable loading formation's share of the load being transmitted to its pads through the set of second balancing beams, which rock to produce the relative movement of the pads in the direction of application of the load. The loading pads may be gimballed so that they can better follow the slopes of the surfaces on which they bear.

Typically, one of the first and second fixtures may be a lower fixture and the other of the first and second fixtures may be an upper fixture. In use the component can then extend substantially horizontally between the fixtures with upward-facing and downward-facing aerofoil surfaces. Such an arrangement allows the lower fixture to support the component during setting up of the rig. For example, the first fixture may be the lower fixture and the second fixture may be the upper fixture.

Conveniently, the first loading formations may provide the outer loading points of the four-point bending arrangement and the second loading formations provide the inner loading points of the four-point bending arrangement. That is, the first loading formations may be spaced a greater distance apart in the spanwise direction of the component than the second loading formations. Particularly when the first fixture is a lower fixture, such an arrangement can improve the support of the component during setting up of the rig.

In a second aspect, the present invention provides the use of the rig according to the first aspect for testing (e.g. fatigue testing) an aerofoil component (e.g. a gas turbine engine blade or vane) in four-point bending by applying a cyclically varying load to opposing aerofoil surfaces of the component.

In a third aspect, the present invention provides a method of testing (e.g. fatigue testing) an aerofoil component (e.g. a gas turbine engine blade or vane) in four-point bending, the method including:
  providing the rig according to the first aspect;
  mounting the component in the rig so that the first and second loading formations are positioned to apply the load to the opposing aerofoil surfaces of the component;
  applying a cyclically varying load to the opposing aerofoil surfaces through the first and second loading formations, whereby the second fixture continuously adjusts so that the second loading formations move relative to each other in the direction of application of the load to balance the load between the loading formations during the cyclical load variation.

The method may have any one or, to the extent that they are compatible, any combination of the following optional features.

In the example when each loading formation has two pads which make loading-contact with that formation's aerofoil surface at respective positions spaced apart in the chordwise direction of the component, the component is mounted so that the pads of each loading formation make loading-contact with that formation's aerofoil surface, and on application of the cyclically varying load, each adjustable loading formation continuously adjusts so that its pads move relative to each other in the direction of application of the load to balance that loading formation's share of the load between the pads during the cyclical load variation.

The aerofoil component may be an organic matrix composite component, such as a component formed of carbon fibre reinforced plastic and/or glass fibre reinforced plastic.

The method may include enclosing the rig in an environmental chamber e.g. for hot or wet testing. Such testing is difficult to perform using conventional forced modal excitation approaches.

BRIEF DESCRIPTION OF THE DRAWINGS

Embodiments of the invention will now be described by way of example with reference to the accompanying drawings in which:

FIG. 1 shows schematically a rig for testing an aerofoil component in four-point bending.

DETAILED DESCRIPTION AND FURTHER OPTIONAL FEATURES OF THE INVENTION

With reference to FIG. 1, a rig for testing an aerofoil component in four-point bending is generally indicated at 10 and has a direction of application of load which is in the vertical direction of the drawing.

The rig has lower (first) fixture 12 and an upper (second) fixture 14. Lower fixture is securely and rigidly mountable to an immovable base, while the upper fixture 14 is movable up and down in the vertical direction, for example by a hydraulic or electrically driven jack or cross-head of a universal testing machine. A gas turbine engine aerofoil component 16, such as a fan blade, is located between the lower and upper fixtures, supported on the lower fixture. The component extends substantially horizontally with its opposing aerofoil surfaces facing upwards and downwards. Guide posts 17 serve to locate component in the correct position on the lower fixture.

The component 16 has a complex shape, which also deforms in a complex and uneven manner under loading. The rig is adapted to be able provide balanced loading during four-point bending, especially during cyclical variation of the four-point bending load.

More particularly, the lower fixture 12 has two first loading formations 18, 20 which are positioned to apply the load to the underside aerofoil surface, the first loading formations being spaced a distance $S_1$ apart in the spanwise direction of the component (i.e. the direction of the component which spans working gas annulus of the engine). Similarly, the upper fixture 14 has two second loading formations 22, 24 which are positioned to apply the load to the topside aerofoil surface, the second loading formations being spaced a distance $S_2$ apart in the spanwise direction of the component. Distance $S_1$ is greater than distance $S_2$, with the first loading formations providing the outer loading points of the four-point bending arrangement and the second loading formations providing the inner loading points of the four-point bending arrangement.

Each loading formation 18, 20, 22, 24 has two gimballed pads 26 which make loading-contact with that formation's aerofoil surface at respective positions spaced a distance C apart in the chordwise direction of the component. By gimballing the pads, they are better able follow the slopes of the surfaces on which they bear during loading.

The upper fixture 14 has a set of first balancing beams 28, with the two second loading formations 22, 24 being at opposite ends of the beams. The load is transmitted from the jack or cross-head through the first balancing beams to the second loading formations. The beams can rock about central pivot points 30 so that the second loading formations move relative to each other in the direction of application of the load, thereby balancing the load between all the loading formations during the cyclical load variation.

One of the first loading formations 18 has a simple support 32 for its pads 26. In contrast, the other first loading formations 20, and the two second loading formations 22, 24 have respective sets of second balancing beams 34 for their pads 26. More particularly, in each of these three loading formations 20, 22, 24, the respective pads are supported at opposite ends of the second balancing beams, which can rock about central pivot points 36 so that the pads move relative to each other in the direction of application of the load, thereby balancing that loading formation's share of the load between the pads during the cyclical load variation. The share of the load of the first loading formation 18 having the simple support 32 is also thereby balanced between its pads 26.

Thus the "tree structure" of the upper fixture 14 in which the load is transmitted to each loading pad 26 via two sets of load balancing beams 28, 34, in combination with the additional set of balancing beams 34 of the first loading formations 20 of the lower fixture 12, balance the load left and right, and front and rear, thereby ensuring that all pads carry equal shares of the load throughout the loading cycle, even as the component deflects asymmetrically and unevenly. In addition, the use of a four-point bending arrangement can ensure that the maximum bending stress occurs in the centre section of the component away from the loading formations 18, 20, 22, 24.

The rig can thus be used to perform fatigue testing in a manner that does not depend on exciting the component's vibration modes, making the rig particularly suitable for testing OMC components. The rig is also compatible with fast set up times, which is desirable when testing many components. In addition, the rig can carry high applied loads, allowing component fatigue failures to be achieved in reasonable time scales. Further, the rig can be enclosed in an environmental chamber, e.g. for hot or wet testing.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A rig for testing an aerofoil component in four-point bending, the aerofoil component having a first aerofoil surface and an oppositely-facing second aerofoil surface, the rig including a first fixture and a second fixture movable relative to each other to apply a cyclically varying load to the first aerofoil surface and the second aerofoil surface of the aerofoil component,
    the first fixture having two first loading formations which are positioned to apply the load to the first aerofoil surface of the component, the two first loading formations being spaced apart in a spanwise direction of the component, and the second fixture having two second loading formations which are positioned to apply the load to the second aerofoil surface of the component, the two second loading formations also being spaced apart in the spanwise direction of the component, the spanwise spacing of the two second loading formations being less than the spanwise spacing of the two first loading formations, and the two second loading formations being positioned relative to the two first loading formations such that the first fixtures and the second fixtures apply the load in a four-point bending arrangement;

wherein the second fixture is configured so that the two second loading formations are movable relative to each other in a direction of application of the load to balance the load between the two second loading formations during the cyclical load variation.

2. The rig according to claim 1, wherein the two second loading formations are supported at opposite ends of a set of first balancing beams of the second fixture, the load being transmitted to the second loading formations through the set of first balancing beams, which rock to produce the relative movement of the two second loading formations in the direction of application of the load.

3. The rig according to claim 1, wherein:
each loading formation has two pads which make loading-contact with that formation's aerofoil surface at respective positions spaced apart in the chordwise direction of the component; and
each of three of the loading formations is configured so that its pads move relative to each other in the direction of application of the load to balance that loading formation's share of the load between the pads during the cyclical load variation.

4. The rig according to claim 3, wherein each of said three loading formations has a respective set of second balancing beams which support that loading formation's pads at opposite ends thereof, each of said three loading formation's share of the load being transmitted to its pads through the set of second balancing beams, which rock to produce the relative movement of the pads in the direction of application of the load.

5. The rig according to claim 3, wherein the pads of the loading formations are gimballed.

6. The rig according to claim 1, wherein,
one of the first fixture and the second fixture is a lower fixture, and the other of the first fixture and the second fixture is an upper fixture,
in use, the component extends substantially horizontally between the lower fixture and the upper fixture with upward-facing and downward-facing aerofoil surfaces.

7. The rig according to claim 6, wherein the first fixture is the lower fixture and the second fixture is the upper fixture.

8. The rig according to claim 1, wherein the first loading formations provide outer loading points of the four-point bending arrangement and the second loading formations provide inner loading points of the four-point bending arrangement.

9. A method of testing an aerofoil component in four-point bending, the method including:
providing the rig according to claim 1;
mounting the component in the rig so that the first loading formations and the second loading formations are positioned to apply the load to the oppositely-facing aerofoil surfaces of the component;
applying a cyclically varying load to the oppositely-facing aerofoil surfaces through the first loading formations and second loading formations, whereby the second fixture continuously adjusts so that the second loading formations move relative to each other in the direction of application of the load to balance the load between the loading formations during the cyclical load variation.

10. The method of testing an aerofoil component according to claim 9, wherein: each loading formation has two pads configured to make loading-contact with that formation's aerofoil surface at respective positions spaced apart in the chordwise direction the component; each of three of the first and second loading formations is configured so that it pads move relative to each other in the direction of application of the load to balance that loading formation's share of load between the pads during the cyclical load variation; the component is mounted so that the pads of each loading formation make load-contact with that formation's aerofoil surface; and on application of the cyclical varying load, each of said three of the first and second loading formations continuously adjust so that it pads move relative to each other in the direction of application of the load to balance that loading formations share of the load between the pads during the cyclical load variation.

11. The method of testing an aerofoil component according to claim 9, wherein the test is a fatigue test.

12. The method of testing an aerofoil component according to claim 9, wherein the aerofoil component is an organic matrix composite component.

13. The rig of claim 1, wherein the two second loading formations are disposed between the two first loading formations in the spanwise direction of the component.

* * * * *